US012569330B2

(12) United States Patent
Rafiee et al.

(10) Patent No.: US 12,569,330 B2
(45) Date of Patent: Mar. 10, 2026

(54) PERCUTANEOUS POTTS SHUNT DEVICES AND RELATED METHODS

(71) Applicant: Transmural Systems LLC, Andover, MA (US)

(72) Inventors: Nasser Rafiee, Andover, MA (US); Alexis Balcom, Andover, MA (US); Mai Le Diep, Andover, MA (US)

(73) Assignee: Transmural Systems LLC, Andover, MA (US)

( * ) Notice: Subject to any disclaimer, the term of this patent is extended or adjusted under 35 U.S.C. 154(b) by 661 days.

(21) Appl. No.: 17/708,147

(22) Filed: Mar. 30, 2022

(65) Prior Publication Data

US 2022/0323196 A1     Oct. 13, 2022

Related U.S. Application Data

(63) Continuation of application No. PCT/US2022/018806, filed on Mar. 3, 2022.

(60) Provisional application No. 63/155,732, filed on Mar. 3, 2021.

(51) Int. Cl.
    *A61F 2/06*      (2013.01)
    *A61L 27/16*     (2006.01)
    *A61L 27/50*     (2006.01)

(52) U.S. Cl.
    CPC .............. *A61F 2/064* (2013.01); *A61L 27/16* (2013.01); *A61L 27/507* (2013.01); *A61F 2250/0029* (2013.01); *A61F 2250/0069* (2013.01); *A61F 2250/0098* (2013.01)

(58) Field of Classification Search
    CPC .............. A61F 2/064; A61F 2250/0029; A61F 2250/0069; A61F 2250/0098; A61L 27/16; A61L 27/507
    See application file for complete search history.

(56) References Cited

U.S. PATENT DOCUMENTS

| | | | |
|---|---|---|---|
| 4,106,129 A | 8/1978 | Carpentier et al. |
| 4,259,753 A | 4/1981 | Liotta et al. |
| 4,666,442 A | 5/1987 | Arru et al. |
| 4,692,164 A | 9/1987 | Dzemeshkevich et al. |
| 5,411,552 A | 5/1995 | Andersen et al. |
| 5,449,384 A | 9/1995 | Johnson |
| 5,606,928 A | 3/1997 | Religa et al. |

(Continued)

FOREIGN PATENT DOCUMENTS

| | | |
|---|---|---|
| EP | 2412397 A1 | 2/2012 |
| JP | 2015519969 A | 7/2015 |

(Continued)

OTHER PUBLICATIONS

International Search Report dated Jun. 16, 2022 in International Patent Application No. PCT/US2022/018806.

(Continued)

*Primary Examiner* — Susan S Su
*Assistant Examiner* — Erin A Kim
(74) *Attorney, Agent, or Firm* — DeWitt LLP; Brian R. Pollack, Esq.

(57) ABSTRACT

The disclosure provides various embodiments of prostheses and delivery systems to permit an interventional cardiologist to create shunts between various blood vessels. Moreover, the disclosed shunts can be used to shunt between various hollow organs, as set forth in the present disclosure.

19 Claims, 13 Drawing Sheets

(56)                    References Cited

U.S. PATENT DOCUMENTS

| | | | |
|---|---|---|---|
| 5,639,278 A | 6/1997 | Dereume et al. | |
| 5,749,921 A | 5/1998 | Lenker et al. | |
| 5,788,715 A | 8/1998 | Watson, Jr. et al. | |
| 5,861,028 A | 1/1999 | Angell | |
| 5,876,432 A * | 3/1999 | Lau | A61F 2/92 |
| | | | 623/1.13 |
| 5,895,410 A | 4/1999 | Forber et al. | |
| 5,928,281 A | 7/1999 | Huynh et al. | |
| 6,059,769 A | 5/2000 | Lunn et al. | |
| 6,090,136 A | 7/2000 | McDonald | |
| 6,106,510 A | 8/2000 | Lunn et al. | |
| 6,238,430 B1 | 5/2001 | Klumb et al. | |
| 6,375,774 B1 | 4/2002 | Lunn et al. | |
| 6,599,303 B1 | 7/2003 | Peterson | |
| 6,602,271 B2 | 8/2003 | Adams et al. | |
| 6,716,231 B1 | 4/2004 | Rafiee et al. | |
| 6,733,525 B2 | 5/2004 | Yang et al. | |
| 6,790,229 B1 | 9/2004 | Berreklouw | |
| 6,797,000 B2 | 9/2004 | Simpson et al. | |
| 6,800,081 B2 | 10/2004 | Parodi | |
| 6,866,677 B2 | 3/2005 | Douk et al. | |
| 6,911,036 B2 | 6/2005 | Douk et al. | |
| 6,926,690 B2 | 8/2005 | Renati | |
| 6,953,476 B1 | 10/2005 | Shalev | |
| 6,960,217 B2 | 11/2005 | Bolduc | |
| 7,044,958 B2 | 5/2006 | Douk et al. | |
| 7,066,946 B2 | 6/2006 | Douk et al. | |
| 7,137,993 B2 | 11/2006 | Acosta | |
| 7,189,259 B2 | 3/2007 | Simionescu et al. | |
| 7,195,641 B2 | 3/2007 | Palmaz et al. | |
| 7,201,772 B2 | 4/2007 | Schwammenthal et al. | |
| 7,294,135 B2 | 11/2007 | Stephens et al. | |
| 7,316,706 B2 | 1/2008 | Bloom et al. | |
| 7,399,315 B2 | 7/2008 | Iobbi | |
| 7,425,219 B2 | 9/2008 | Quadri | |
| 7,442,204 B2 | 10/2008 | Schwammenthal et al. | |
| 7,442,207 B2 | 10/2008 | Rafiee | |
| 7,445,631 B2 | 11/2008 | Salahieh et al. | |
| 7,481,838 B2 | 1/2009 | Carpentier et al. | |
| 7,491,232 B2 | 2/2009 | Bolduc et al. | |
| 7,524,330 B2 | 4/2009 | Berreklouw | |
| 7,655,040 B2 | 2/2010 | Douk et al. | |
| 7,682,352 B2 | 3/2010 | Rafiee et al. | |
| 7,699,892 B2 | 4/2010 | Rafiee et al. | |
| 7,716,801 B2 | 5/2010 | Pouk et al. | |
| 7,753,840 B2 | 7/2010 | Simionescu et al. | |
| 7,753,949 B2 | 7/2010 | Lamphere et al. | |
| 7,780,726 B2 | 8/2010 | Seguin | |
| 7,799,069 B2 | 9/2010 | Bailey et al. | |
| 7,806,917 B2 | 10/2010 | Xiao | |
| 7,806,919 B2 | 10/2010 | Bloom et al. | |
| 7,815,673 B2 | 10/2010 | Bloom et al. | |
| 7,947,072 B2 | 5/2011 | Yang et al. | |
| 7,955,384 B2 | 6/2011 | Rafiee et al. | |
| 7,972,370 B2 | 7/2011 | Douk et al. | |
| 7,998,188 B2 | 8/2011 | Zilla et al. | |
| 8,002,825 B2 | 8/2011 | Letac et al. | |
| 8,052,750 B2 | 11/2011 | Tuval et al. | |
| 8,062,355 B2 | 11/2011 | Figulla et al. | |
| 8,070,802 B2 | 12/2011 | Lamphere et al. | |
| 8,092,518 B2 | 1/2012 | Schreck | |
| 8,092,520 B2 | 1/2012 | Quadri | |
| 8,092,524 B2 | 1/2012 | Nugent et al. | |
| 8,226,710 B2 | 7/2012 | Nguyen et al. | |
| 8,252,051 B2 | 8/2012 | Chau et al. | |
| 8,308,798 B2 | 11/2012 | Pintor et al. | |
| 8,337,541 B2 | 12/2012 | Quadri et al. | |
| 8,348,995 B2 | 1/2013 | Tuval et al. | |
| 8,348,996 B2 | 1/2013 | Tuval et al. | |
| 8,353,954 B2 | 1/2013 | Cai et al. | |
| 8,353,955 B2 | 1/2013 | Styrc et al. | |
| 8,518,096 B2 | 8/2013 | Nelson | |
| 10,426,482 B2 * | 10/2019 | Rafiee | A61F 2/064 |
| 2001/0021872 A1 | 9/2001 | Bailey et al. | |
| 2002/0032481 A1 | 3/2002 | Gabbay | |

| | | | |
|---|---|---|---|
| 2002/0138138 A1 | 9/2002 | Yang | |
| 2003/0055495 A1 | 3/2003 | Pease et al. | |
| 2003/0065386 A1 | 4/2003 | Weadock | |
| 2003/0097172 A1 | 5/2003 | Shalev et al. | |
| 2004/0087998 A1 | 5/2004 | Lee et al. | |
| 2004/0127916 A1 | 7/2004 | Bolduc et al. | |
| 2005/0038508 A1 | 2/2005 | Gabbay | |
| 2005/0043790 A1 | 2/2005 | Seguin | |
| 2005/0049675 A1 | 3/2005 | Wallace | |
| 2005/0055082 A1 | 3/2005 | Ben-Muvhar et al. | |
| 2005/0137769 A1 | 6/2005 | Salahieh et al. | |
| 2005/0143809 A1 | 6/2005 | Salahieh et al. | |
| 2005/0177180 A1 | 8/2005 | Kaganov et al. | |
| 2005/0288706 A1 | 12/2005 | Widomski et al. | |
| 2006/0085012 A1 | 4/2006 | Dolan | |
| 2006/0106449 A1 | 5/2006 | Ben-Muvhar | |
| 2006/0106450 A1 | 5/2006 | Ben-Muvhar | |
| 2006/0173537 A1 | 8/2006 | Yang et al. | |
| 2007/0043435 A1 | 2/2007 | Seguin et al. | |
| 2007/0067029 A1 | 3/2007 | Gabbay | |
| 2007/0250160 A1 | 10/2007 | Rafiee | |
| 2007/0255398 A1 | 11/2007 | Yang et al. | |
| 2007/0288089 A1 | 12/2007 | Gurskis et al. | |
| 2007/0293942 A1 | 12/2007 | Mizraee | |
| 2008/0015687 A1 | 1/2008 | Lashinski et al. | |
| 2008/0021537 A1 | 1/2008 | Ben-Muvhar et al. | |
| 2008/0065191 A1 | 3/2008 | Bolduc et al. | |
| 2008/0077234 A1 | 3/2008 | Styrc | |
| 2008/0125860 A1 | 5/2008 | Webler et al. | |
| 2008/0208328 A1 | 8/2008 | Antocci et al. | |
| 2008/0221672 A1 | 9/2008 | Lamphere et al. | |
| 2009/0005863 A1 | 1/2009 | Goetz et al. | |
| 2009/0062841 A1 | 3/2009 | Amplatz et al. | |
| 2009/0270966 A1 | 10/2009 | Douk et al. | |
| 2009/0270976 A1 | 10/2009 | Douk et al. | |
| 2009/0306768 A1 | 12/2009 | Quadri | |
| 2009/0319038 A1 | 12/2009 | Gurskis et al. | |
| 2010/0036479 A1 * | 2/2010 | Hill | A61F 2/2418 |
| | | | 623/1.26 |
| 2010/0082094 A1 | 4/2010 | Quadri et al. | |
| 2010/0100167 A1 | 4/2010 | Bortlein et al. | |
| 2010/0174363 A1 | 7/2010 | Castro | |
| 2010/0179648 A1 | 7/2010 | Richter et al. | |
| 2010/0179649 A1 | 7/2010 | Richter et al. | |
| 2010/0185275 A1 | 7/2010 | Richter et al. | |
| 2010/0249923 A1 | 9/2010 | Alkhatib et al. | |
| 2010/0262232 A1 | 10/2010 | Annest | |
| 2010/0280606 A1 | 11/2010 | Naor | |
| 2010/0298931 A1 | 11/2010 | Quadri et al. | |
| 2011/0112632 A1 | 5/2011 | Chau et al. | |
| 2011/0137409 A1 | 6/2011 | Yang et al. | |
| 2011/0172784 A1 | 7/2011 | Richter et al. | |
| 2011/0282438 A1 | 11/2011 | Drews et al. | |
| 2011/0313515 A1 | 12/2011 | Quadri et al. | |
| 2011/0319988 A1 * | 12/2011 | Schankereli | A61F 2/2418 |
| | | | 623/2.11 |
| 2011/0319989 A1 | 12/2011 | Lane et al. | |
| 2012/0022639 A1 | 1/2012 | Hacohen | |
| 2012/0059450 A1 | 3/2012 | Chiang et al. | |
| 2012/0065652 A1 | 3/2012 | Cully et al. | |
| 2012/0078353 A1 | 3/2012 | Quadri et al. | |
| 2012/0078360 A1 | 3/2012 | Rafiee | |
| 2012/0179244 A1 | 7/2012 | Schankereli et al. | |
| 2012/0215303 A1 | 8/2012 | Quadri et al. | |
| 2012/0316642 A1 | 12/2012 | Yu et al. | |
| 2012/0323316 A1 * | 12/2012 | Chau | A61F 2/24 |
| | | | 623/2.37 |
| 2014/0018906 A1 | 1/2014 | Rafiee | |
| 2014/0039083 A1 | 2/2014 | Krepski et al. | |
| 2014/0128965 A1 | 5/2014 | Rafiee | |
| 2014/0163668 A1 | 6/2014 | Rafiee | |
| 2014/0358223 A1 | 12/2014 | Rafiee et al. | |
| 2015/0134051 A1 | 5/2015 | Donadio et al. | |
| 2019/0231510 A1 * | 8/2019 | Rafiee | A61L 27/507 |

FOREIGN PATENT DOCUMENTS

| | | | |
|---|---|---|---|
| KR | 20130110413 A1 | 10/2013 | |
| KR | 101501614 B1 | 3/2015 | |

(56)                    References Cited

FOREIGN PATENT DOCUMENTS

| RU | 100 718 U1 | 12/2010 |
| WO | WO2007121314 A2 | 10/2007 |
| WO | WO2012061809 A2 | 5/2012 |
| WO | WO2013131069 A1 | 9/2013 |
| WO | WO2015069947 A1 | 5/2015 |
| WO | WO2015148821 A1 | 10/2015 |

OTHER PUBLICATIONS

Written Opinion of the International Searching Authority dated May 17, 2022 in International Patent Application No. PCT/US2022/018806.

International Search Report, for related application No. PCT/US2011/059586, mailed May 25, 2012.

International Preliminary Report on Patentability and Written Opinion, or related application No. PCT/US2011/059586, mailed May 25, 2012.

BioIntegral Surgical, Mitral Valve Restoration System.

International Search Report for co-pending international application No. PCT/US2013/028774, mailed Jun. 14, 2013.

International Preliminary Report on Patentability and Written Opinion, on related application No. PCT/US2014/064431 mailed Mar. 26, 2015.

International Search Report, for related application No. PCT/US2015/022782, mailed Jun. 18, 2015.

International Search Report and Written Opinion in Application No. PCT/US2016/052005, mailed Dec. 29, 2016.

International Search Report and Written Opinion in Application No. PCT/US2018/049373, mailed Dec. 6, 2018.

Office Action in related Japanese Patent Application No. JP2018-514884 dated Jun. 30, 2020 with English language translation.

* cited by examiner

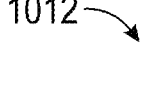
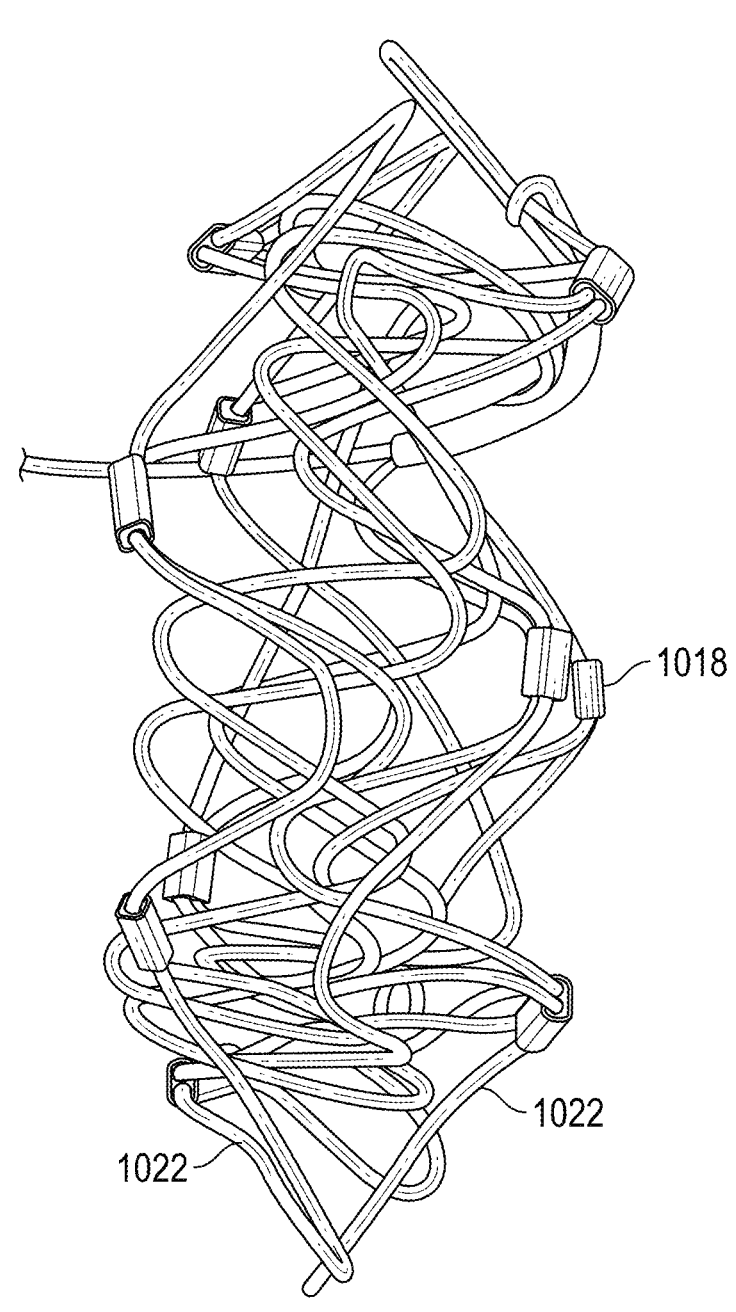
FIG. 1B

1112
1121
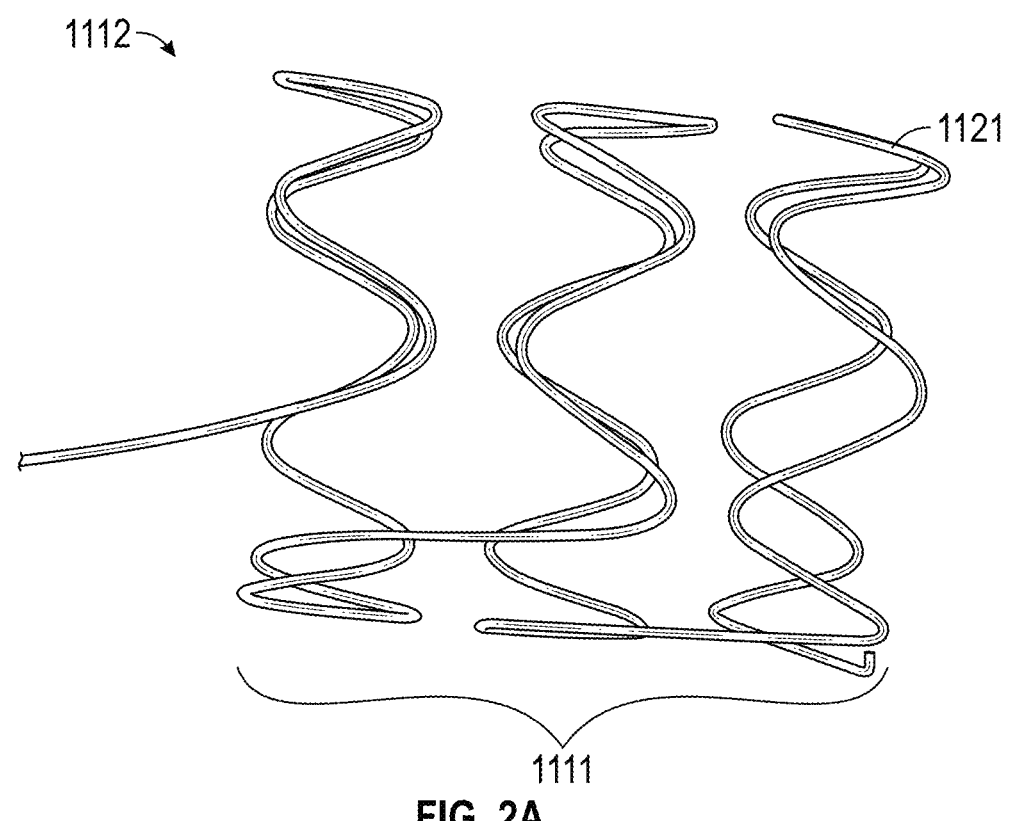
1111
FIG. 2A
1110
1114
1124
1112
1126
FIG. 2B
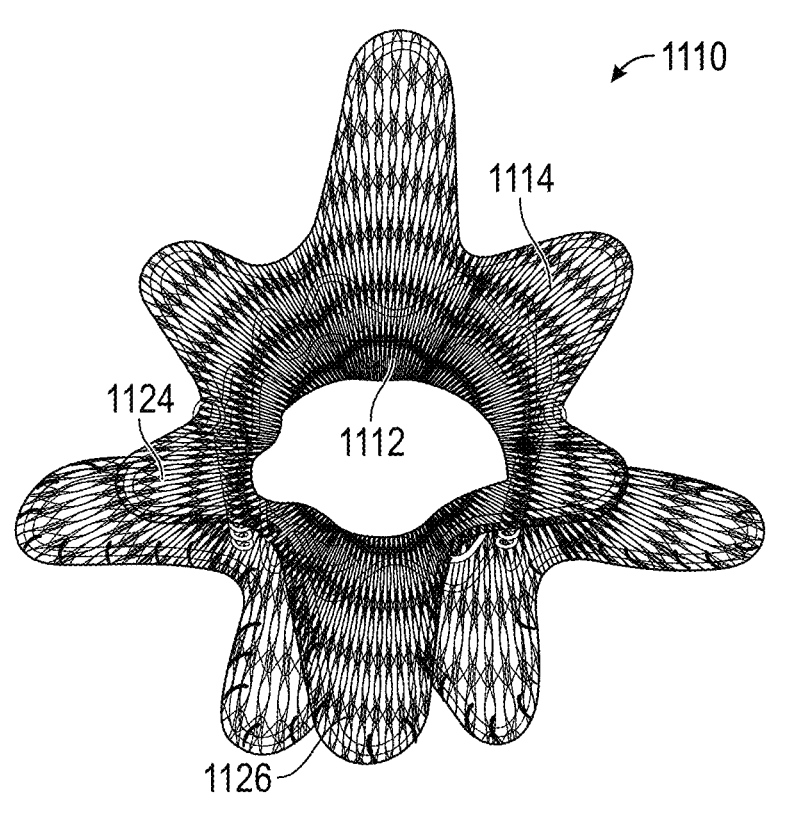

1210

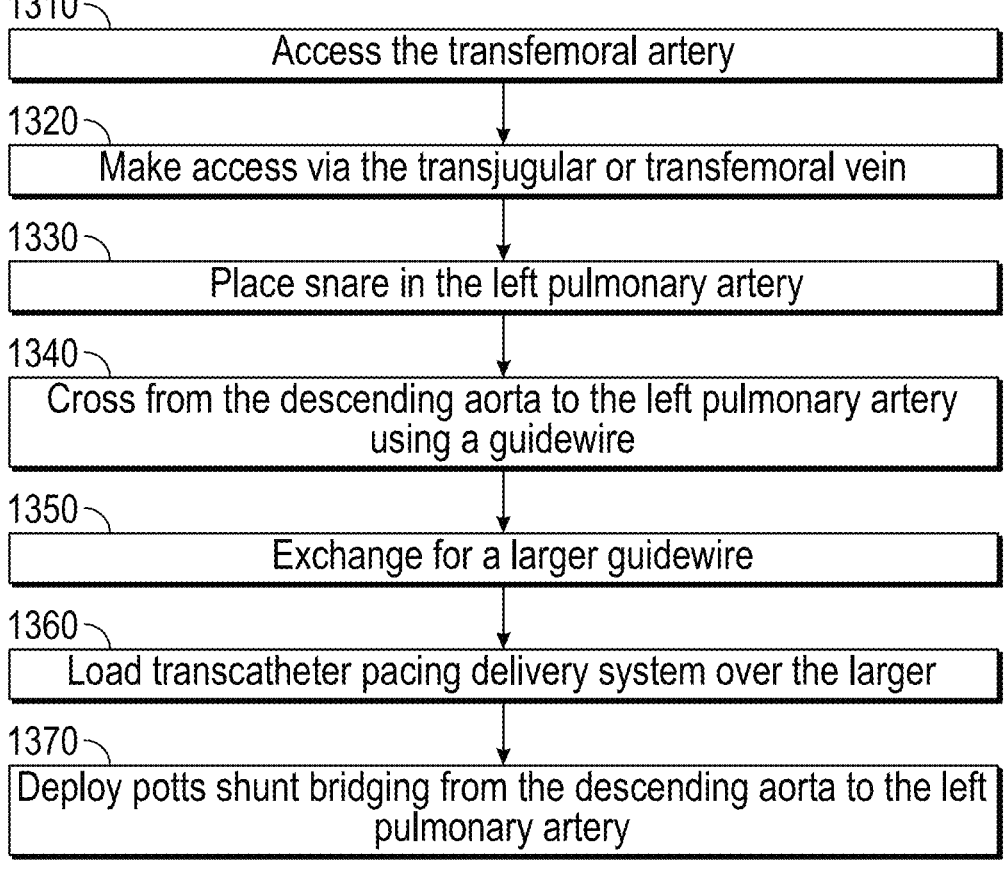

1310 ─┐
Access the transfemoral artery

1320 ─┐
Make access via the transjugular or transfemoral vein

1330 ─┐
Place snare in the left pulmonary artery

1340 ─┐
Cross from the descending aorta to the left pulmonary artery
using a guidewire 1350 ─┐
Exchange for a larger guidewire 1360 ─┐
Load transcatheter pacing delivery system over the larger 1370 ─┐
Deploy potts shunt bridging from the descending aorta to the left
pulmonary artery

FIG. 11

PERCUTANEOUS POTTS SHUNT DEVICES AND RELATED METHODS

CROSS-REFERENCE TO RELATED APPLICATIONS

The present patent application claims the benefit of priority to and is a continuation of International Patent Application No. PCT/US2022/018806, filed Mar. 3, 2022, which in turn claims the benefit of priority to U.S. Provisional Patent Application No. 63/155,732, filed Mar. 3, 2021. The present patent application is related to U.S. patent application Ser. No. 16/264,402, filed Jan. 31, 2019, which is a continuation of and claims the benefit of priority to International Application No. PCT/US2018/49373, filed Sep. 4, 2018, which in turn claims the benefit of priority to U.S. Provisional Patent Application Ser. No. 62/553,532, filed Sep. 1, 2017, U.S. Provisional Patent Application Ser. No. 62/615,330, filed Jan. 9, 2018, U.S. Provisional Patent Application Ser. No. 62/615,433, filed Jan. 9, 2018, and U.S. Provisional Patent Application Ser. No. 62/664,722, filed Apr. 30, 2018. The present patent application is also related to U.S. patent application Ser. No. 15/267,075, filed Sep. 15, 2016. Each of the foregoing patent applications is incorporated by reference herein for any purpose whatsoever.

FIELD OF THE DISCLOSURE

The present disclosure relates to devices and methods for transcatheter (i.e., performed through the lumen of a catheter) Potts shunt systems for nonsurgical, percutaneous extra-anatomic bypass between two adjacent vessels and/or organs.

BACKGROUND

Pulmonary hypertension of diverse etiologies causes severe symptoms and have a high mortality rate. Symptoms include inability to exercise, shortness of breath, right-sided congestive heart failure, and sudden death. New pharmacologic options have significantly prolonged survival in adults with severe pulmonary hypertension. These therapeutic options have led to nationwide centers of excellence for the care of pulmonary hypertension. Despite successful pharmacotherapy, the disease progresses in the majority causing progressive right ventricular failure and declining functional status. Heart-lung transplantation may not be an option. The present disclosure provides improvements over the state of the art.

SUMMARY OF THE DISCLOSURE

The purpose and advantages of the present disclosure will be set forth in and become apparent from the description that follows. Additional advantages of the disclosed embodiments will be realized and attained by the methods and systems particularly pointed out in the written description hereof, as well as from the appended drawings.

A Potts shunt is a side-to-side connection from the left pulmonary artery to the descending aorta that can be used to treat severe pulmonary hypertension. More specifically, a Potts shunt can be used to divert some of the high pressure pulmonary blood to escape out to the body without having to through damaged lungs.

Forming a Potts shunt (between the left pulmonary artery and the descending thoracic aorta) is a surgical procedure that can divert blood flow to relieve right heart failure in patients with end-stage pulmonary hypertension. It can be offered as a bridge to transplantation or as a destination therapy. A traditional surgical Potts shunt is complex and presents numerous risks.

Children born with single ventricle physiology (SVP), a form of cyanotic congenital heart disease (CCHD), represent 7.7% of all congenital heart disease patients and have a birth incidence of approximately 4-8 per 10,000. In the United States, this represents approximately 2,000 children born each year. Currently, SVP infants undergo a series of staged surgical procedures. The first palliative procedure establishes a balance between systemic and pulmonary output while minimizing the overload on the single ventricle. The following palliative procedure is often cavopulmonary anastomosis through a bidirectional Glenn shunt or hemi-Fontan procedure to allow for passive pulmonary bloodflow. These are surgical procedures that are invasive and traumatic, requiring significant recuperation time and excessive burden on such a young patient.

A transcatheter approach for obtaining the results of the surgical procedures described above can revolutionize the management of patients with severe pulmonary hypertension and/or congenital heart disease. A nonsurgical transcatheter intervention can limit the burden of surgery while also reducing cost. There is a considerable unmet need for a purpose-built cavopulmonary anastomosis device. To Applicant's knowledge no commercial alternatives exist for off-label medical use.

In some embodiments, a percutaneously deliverable tubular Potts prosthesis to permit an interventional cardiologist to create a shunt between the left pulmonary artery to the descending aorta is provided. The prosthesis may comprise a structural frame portion (also referred to simply as a frame) and a membrane (also referred to as a fabric) over- and/or under-lying the frame portion. The prosthesis may be collapsible and may comprise a collapsible coil forming a length of the prosthesis. The membrane may be, for example, a woven or non-woven fabric. The membrane may comprise an expanded polytetrafluorethylene material, and/or may comprise biological tissue material. In various embodiments, the prosthesis may include tabs or projections and/or folding lateral wings or paddles. The projections may include one or more radiopaque markers formed thereon. Such radiopaque markers may be provided at any location on the projection. In one embodiment, radiopaque markers are provided on the outward lateral tip of the farthest laterally extending projections. The ends of the prosthesis including the projections may be referred to as crowns and may form a seal against the blood vessel.

In some implementations, a tubular prosthesis is provided that includes an elongate compliant tubular body having a proximal end and a distal end, a distal sealing flange coupled to the distal end of the elongate compliant tubular body, the distal sealing flange being configured and arranged to facilitate seating the tubular prosthesis against a first concave vessel wall of a first vessel, wherein the tubular prosthesis is configured to extend outwardly through an ostium formed in the first concave vessel wall when deployed. The distal sealing flange remains inside the ostium after deployment. The tubular prosthesis further includes at least one (and preferably two, or three) laterally extending projection that is structurally distinct from the distal sealing flange and extends radially outwardly with respect to the distal sealing flange. The laterally extending projection(s) and flange can be provided on both the proximal and distal ends of the prosthesis. The laterally extending projection can extend radially outwardly between two radial extensions of each of the proximal and distal flanges. The at least one laterally extending projection is located proximate the distal sealing flange, and extends laterally (and radially outwardly) beyond the distal sealing flange. The at least one laterally extending projection is configured and arranged to resist being pulled through said ostium, and provides a second mechanism to resist pull-through, and supplements the function of the distal sealing flange.

Preferably, the at least one laterally extending projection includes two or three laterally extending projections that are oriented about 180 degrees in the case of two such projections, or 120 degrees in the case of three such projections, about a longitudinal axis of the tubular prosthesis. The laterally extending projections are preferably configured and arranged to rest near a bottom of the first concave vessel wall next to the ostium. Also, in some implementations a first end of the prosthesis can be provided with a pair of such projections that are separated by 180 degrees, and the second end of the prosthesis can be provided with three evenly spaced projections at its respective flange. During installation, the first end of the prosthesis or shunt can be oriented toward the distal end of the delivery catheter, and can be oriented upon delivery such that the projections align with the direction of blood flow and sit at a "bottom" of the concavity of the vessel into which they are deployed. The second end of the prosthesis, which is therefore oriented toward a proximal direction (toward the proximal end of the delivery catheter) can then be deployed within the second vessel, which can be expected to be oriented obliquely with respect to the first vessel. The proximal end of the shunt is preferably provided with three evenly spaced projections to facilitate preventing the projections from being oriented orthogonally with respect to the blood flow. In other words, preferably, one of the projections is oriented along the direction of the bloodflow in the second vessel. Providing three evenly spaced projections on the proximal end helps avoid the need for twisting the prosthesis about its central axis to get two diametrically opposed projections to both lay along the direction of the blood flow. Similarly, both ends of the prosthesis can be provided with three such projections, spaced 120 apart from each other about the central longitudinal axis of the prosthesis. In this manner, deploying both ends of the prosthesis is simplified as it is less critical to ensure alignment of any of the projections with the blood flow in either vessel.

The laterally extending projections are configured and arranged to prevent the distal end of prosthesis from being pulled proximally through the ostium. The laterally extending projections can be directly or indirectly connected to a framework of the tubular prosthesis disposed proximally with respect to the distal sealing flange. For example, the laterally extending projections can be integrated into a circumferential ring structure that forms a distal end portion of the prosthesis. The circumferential ring structure typically includes an undulating wire that circumferentially traverses a circumference of the tubular prosthesis. The undulating can be defined by a serpentine pattern along at least a part of its length that can have various shapes, such as a sinusoidal shape, a sawtooth shape, a curved wave shape, and the like. One or both of the laterally extending projections can be formed from the same undulating wire that forms the circumferential ring structure.

In some implementations, the circumferential ring structure is formed from an undulating wire that transitions from a serpentine pattern along a first end face of the tubular prosthesis into a first of the two laterally extending projections, transitions from the first of the two laterally extending projections back into the serpentine pattern along a second end face of the tubular prosthesis opposite to the first lateral side of the tubular prosthesis, transitions from the serpentine pattern into the second of the two laterally extending projections along the second circumferential face of the tubular prosthesis, and transitions from the second of the two laterally extending projections back to the serpentine pattern along the first end face of the tubular prosthesis.

In some implementations of the tubular prosthesis, a membrane can be configured to cover the inside and/or outside of the elongate compliant tubular body and the distal flange. For example, the membrane can include a woven or non-woven fabric. If desired, the membrane can include an expanded polytetrafluoroethylene ("ePTFE") material, and/or biological tissue material. If desired, the laterally extending projection(s) may, or may not be covered by the membrane. In some embodiments, the laterally extending projection(s) can include at least one radiopaque marker formed thereon. For example, each of the two or three laterally extending projections at either end of the Potts shunt disclosed herein can include at least one radiopaque marker formed thereon at a location that resides at the ostium during implantation near the base of each of the laterally extending projections, such as at the apex or outermost extent of the projection. In some embodiments, the laterally extending projection(s) can extend from a location proximal to the distal sealing flange to a location that is distal with respect to the distal sealing flange, and if desired, the laterally extending projection(s) can extend from a location distal to the proximal sealing flange to a location that is proximal with respect to the proximal sealing flange.

In some implementations of the tubular prosthesis, the distal and/or proximal sealing flange can be formed at least in part from an undulating, star-shaped circumferential wire frame (having six points, for example) that is structurally distinct from and located adjacent the circumferential ring structure. The undulating star-shaped circumferential wire frame of the distal and/or proximal flange can be coupled to the circumferential ring structure at a respective longitudinal end of the circumferential ring structure. The undulating, star-shaped circumferential wire frame of the distal and/or proximal flange can be coupled to the circumferential ring structure by a plurality of fabric filaments, wherein the star-shaped circumferential wire frame of the distal and/or proximal flange is able to move with respect to the circumferential ring structure. If desired, the undulating, star-shaped circumferential wire frame of the distal and/or proximal flange can be coupled to the membrane (such as by stitching and/or adhesive or weaving), and further wherein the circumferential ring structure can be coupled to the membrane. The star-shaped circumferential wire frame of the distal and/or proximal flange can be configured to move or flex with respect to the circumferential ring structure.

In some embodiments, the elongate compliant tubular body can be formed from a one, or a plurality of, longitudinally spaced undulating circumferential wire frames (formed into a zig-zag pattern, for example, having changes in direction at the proximal and distal ends of the wire frame(s)) that are attached to a tubular membrane material. If desired, successive undulating circumferential wire frames (or strut rings), if more than one is used, are circumferentially aligned so that they can nest along an axial direction to facilitate bending and shortening (axial collapse) of the prosthesis.

As alluded to above, the tubular prosthesis can further include a proximal sealing flange coupled to the proximal end of the elongate compliant tubular body. The proximal sealing flange can be configured and arranged to facilitate seating of the tubular prosthesis against a second concave vessel wall, wherein the tubular prosthesis is configured to extend outwardly through a second ostium formed in the second concave vessel wall when deployed. The proximal sealing flange is configured to remain inside the vessel by the second ostium after deployment. The prosthesis can further include at least one, two, three or more laterally extending projection(s) that are structurally distinct from the proximal sealing flange, which may be star shaped, having three, four, five, or six points, for example, as described above.

In some implementations, the tubular prosthesis is configured and arranged to self-expand radially outwardly when not constrained. In some embodiments, the tubular prosthesis is configured and arranged to be expanded by an inflatable member of a delivery catheter, for example. In some embodiments, the proximal end of the elongate compliant tubular body can be outwardly flared or bell-shaped to enhance apposition against an interior wall of a second vessel. If desired the tubular prosthesis can define at least one fenestration through a sidewall thereof to permit leakage of bodily fluid through the fenestration.

In some embodiments, the prosthesis can include a membrane that in turn includes an inner layer and an outer layer that cover the inner and outer surfaces of a framework of the prosthesis. In some implementations, the prosthesis can further include at least one elastic body that causes the tubular prosthesis to shorten in length when unconstrained. The at least one elastic body can include at least one tension coil spring that defines a lumen along its length. A central longitudinal axis of the at least one tension coil spring is preferably co-incident with, parallel to and offset with, or concentric with a longitudinal axis of the prosthesis. Thus, the tubular prosthesis can be of adjustable telescoping length. Preferably, the inside diameter of the prosthesis remains substantially unchanged when the prosthesis is adjusted in length. The at least one tension coil spring can actually include a plurality of tension coil springs that may be adjacent to or concentrically located with respect to one another. For example, one, two or three (or more) tension springs can be coupled to the framework of the prosthesis to cause it to shorten unless stretched axially. The springs can be located over or underneath a fabric layer that is disposed along an inside and/or outside surface area of the shunt structure.

The disclosure further provides a delivery system including any of the prostheses described elsewhere herein mounted thereon, wherein the prosthesis is mounted on a longitudinal inner member and inside of a retractable sheath. The delivery system can further include at least one removable tether having a first end and a second end. The first and second ends of the tether can be routed through a portion of the prosthesis and extend proximally through and out of a proximal region of the delivery system. The delivery system can further include a first set of radiopaque markers near the distal end of the delivery system, and a second set of markers that are visible outside the patient during a procedure that indicates the relative position of the delivery system and prosthesis. The first and second set of markers can be configured to be maintained in registration with each other during the procedure. For example, the first set of markers can be located on a distal atraumatic tip of the delivery system made of iron oxide to facilitate navigation under MRI or other imaging modality to position the delivery system accurately, and wherein the second set of markers can indicate the relative longitudinal position of the portions of the delivery system. If desired, the markers can be configured to indicate when the distal sealing flange of the prosthesis is suitably configured to pull against an inner face of the wall of a lumen.

The disclosure further provides a delivery system that includes an elongate inner core member having a proximal end and a distal end, the distal end having a compliant atraumatic tip mounted thereon, an inflatable member mounted on the elongate inner core member, a prosthesis as described elsewhere herein mounted around the elongate inner core member, and a retractable sheath having a proximal end and a distal end. The retractable sheath is slidably disposed with respect to, and depending on its position along the elongate core member, selectively covers, the prosthesis and at least a part of the inflatable member. The delivery system can further include a first actuator configured and arranged to advance the sheath proximally with respect to the elongate inner core, inflatable member, and prosthesis, and, a second actuator coupled to a reservoir of fluid. The reservoir is fluidly coupled to the inflatable member, and actuating the second actuator causes the fluid to flow out of the reservoir into the inflatable member to cause the inflatable member to expand radially outwardly.

In some embodiments, the prosthesis is mounted at least partially over and surrounding the inflatable member. For example, a distal portion of the prosthesis can be mounted over the inflatable member, a proximal portion of the prosthesis can be mounted over the inflatable member, or a central portion of the prosthesis can be mounted over the inflatable member. If desired, the prosthesis can be mounted on the elongate inner core member proximally, or distally, with respect to the inflatable member.

In some embodiments, the compliant atraumatic tip can include a gradually tapering distal section that transitions from a larger proximal diameter to a smaller distal diameter. The compliant atraumatic tip can further include a gradually tapering proximal section that transitions from a smaller proximal diameter to a larger distal diameter. A distal end of the proximal section of the compliant atraumatic tip can abut a proximal end of the distal section of the compliant atraumatic tip.

The disclosure further provides methods of delivering and implanting a tubular prosthesis. The method includes providing a delivery system as described herein, delivering a distal end of the delivery system to a target location through the ostium of the first concave vessel wall, withdrawing the sheath proximally to expose the prosthesis, positioning the distal end of the prosthesis in the ostium so that a first sealing flange and the at least one laterally extending projection are inside the first concave vessel wall and the elongate compliant tubular body extends through the ostium outside of the first vessel, actuating the second actuator to cause the inflatable member to expand, and expanding the distal end of the tubular prosthesis using the balloon to fit it into the ostium and to shape the sealing flange to fit against the first concave vessel wall. This procedure can be repeated at the opposing end of the prosthesis to seat the second flange in a second vessel.

It is to be understood that both the foregoing general description and the following detailed description are exemplary and are intended to provide further explanation of the embodiments disclosed herein.

The accompanying drawings, which are incorporated in and constitute part of this specification, are included to illustrate and provide a further understanding of the method and system of the disclosure. Together with the description, the drawings serve to explain the principles of the disclosed embodiments.

BRIEF DESCRIPTION OF THE DRAWINGS

The foregoing and other objects, aspects, features, and advantages of exemplary embodiments will become more apparent and may be better understood by referring to the following description taken in conjunction with the accompanying drawings, in which:

FIGS. 1A and 1B, illustrate a the structural frame of a prosthesis for a Potts shunt, in accordance with an embodiment of the disclosure.

FIG. 2A illustrate a the structural frame of a prosthesis for a Potts shunt, in accordance with an embodiment of the disclosure.

FIGS. 2B, and 2C illustrate the prosthesis for a Potts shunt of FIG. 2A.

FIG. 11 illustrates a block diagram of a method for placing a Potts shunt, in accordance with one implementation.

DETAILED DESCRIPTION

Figure 1A:
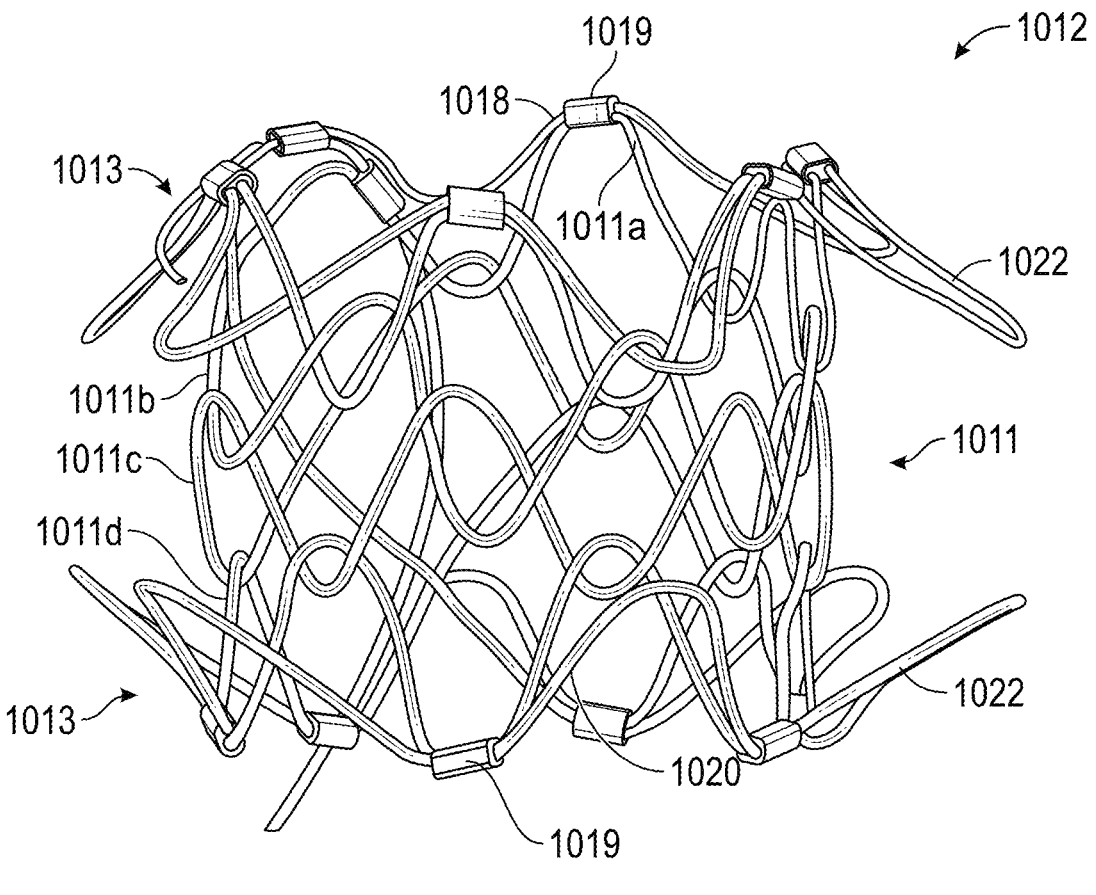

Reference will now be made in detail to the present preferred embodiments of the disclosure, examples of which are illustrated in the accompanying drawings. The methods and corresponding steps of the disclosed embodiments will be described in conjunction with the detailed description of the systems. The exemplary embodiments illustrated herein can be used to perform Potts shunting procedures as well as other types of shunting procedures, but in a percutaneous manner.

Further, it is to be appreciated that the disclosed embodiments, or variations thereof, can be used for a multitude of procedures involving the connection of blood vessels or other biological lumens to native or artificial structures. Such endograft devices represent a potential breakthrough for physicians and patients, especially for young patients who require a safe, less-burdensome, and effective alternative to open heart surgery: a percutaneous approach to heal congenital heart failure.

Cardiovascular shunts are bypass conduits that can be used to connect two blood vessels—for example, two arteries, an artery and a vein, or two veins. The goal of such connection may be to equalize blood pressure between the two blood vessels, for example. Exemplary procedures using cardiovascular shunts include Potts procedures. In some situations, these procedures can be used in pediatric applications to address structural issues.

Potts procedures are palliative procedures that improve pulmonary blood flow. A Potts procedure includes forming a Potts shunt between the left pulmonary artery and the descending thoracic aorta. The Potts shunt can be used to divert blood flow to relieve right heart failure in patients with end-stage pulmonary hypertension. It can be offered as a bridge to transplantation or as a destination therapy. A traditional surgical Potts shunt installation is complex procedure and presents numerous risks.

In accordance with the present disclosure, implementations of a catheter-based Potts shunt is provided. The catheter-based shunt can be delivered by way of a delivery system as set forth herein and used to shunt the left pulmonary artery to the descending thoracic aorta. The Potts shunt may comprise a percutaneously deliverable tubular prosthesis to permit an interventional cardiologist to create a shunt between the descending aorta and the left pulmonary artery. The implant can provide an urgently needed option for patients with severe pulmonary hypertension and/or with congenital heart failure to avoid the burden of a three-stage surgery (so called palliative surgery), the burden of an additional heart transplantation after failure of the palliative surgeries, or of the lifelong medication intake after direct heart transplantation.

More generally, the present disclosure relates to a catheter system and associated prosthesis to allow traversal from a donor blood vessel to a recipient blood vessel. For example, a catheter system to allow traversal from the left pulmonary artery to the descending aorta is provided. The present disclosure further relates to a catheter traversal system between the donor blood vessel and the recipient blood vessel using, for example, transcatheter electrosurgery techniques. The system may be configured to establish donor and recipient side-to-side anastomoses and/or shunting, secure from extravasation, in a range of expected anatomies in patient requiring a Potts shunt for severe pulmonary artery hypertension. The system may be used for both adjacent and non-adjacent donor/recipient pairs.

The system and prosthesis may generally be characterized as:

Sufficiently resistive to allow patient-tailored shunting that balances decompressive flow against excessive shunting causing lower extremity hypoxemia.

Not causing hemodynamically significant obstruction in either the donor vessel or the recipient vessel.

Resisting inadvertent operator "pull-through" from both donor and recipient vessels.

Conspicuous under the intended image-guidance modality; MRI compatibility is desirable.

Addressing mural recoil, kinking, and motion throughout the cardiac and respiratory cycles.

Accommodating growing children by allowing late post-dilation to adult vessel dimensions (ultimately dilatable to adult size vessels). Thus, after installation, in some implementations, the shunts can be dilated after the patient has grown to permit additional blood flow through the shunt.

Shunts provided herein thus provide an anastomosis between adjacent blood vessels. The so formed anastomosis is resistant to inadvertent separation and pull-through, hemorrhage, thrombosis, neointimal overgrowth, angulation, distortion, or failure by patient and cardiovascular motion.

In accordance with one embodiment, a prosthesis for shunt procedures is provided having an elongate compliant tubular body with a proximal end and a distal end. A distal and/or proximal sealing flange, also referred to herein as a crown or star shaped flange, can be coupled to or be integral with the respective distal and/or proximal end of the elongate compliant tubular body. The proximal and/or distal sealing flange comprises a plurality of projections extending laterally away from the tubular body and is configured and arranged to facilitate seating the tubular prosthesis against a concave vessel wall of a vessel, wherein the tubular prosthesis is configured to extend outwardly through an ostium formed in the concave vessel wall when deployed, and wherein the proximal and/or distal sealing flange remains inside the concave vessel after deployment. In some embodiments, the prosthesis may further include at least one laterally extending projection proximate the proximal and/or distal flanges, also referred to as a paddle, that is configured and arranged to resist being pulled through said ostium. The paddle(s) extend laterally away from the tubular body a distance further than the extension of the projections of the respective proximal and/or distal flange. The paddle(s) may be a part of the sealing flange or may be separate from the sealing flange.

In accordance with various embodiments, the prosthesis comprises a structural frame portion (also referred to simply as a frame) and a membrane (also referred to as a fabric or cellular material) over- and/or under-lying the frame portion. The prosthesis may be collapsible and may comprise a collapsible coil forming a length of the prosthesis, or one or more tension coil springs can be used adjacent one or more strut rings that form the tubular body of the prosthesis. The membrane may be, for example, a woven or non-woven fabric. The membrane may comprise an expanded polytetrafluorethylene material, and/or may comprise biological tissue material. In various embodiments, the prosthesis may include tabs or projections and/or folding lateral wings or paddles. The projections may include one or more radiopaque markers formed thereon, such as at the outermost extremity thereof. Such radiopaque markers may be provided at any location on the projection. In one embodiment, radiopaque markers are provided on the outward lateral tip of the farthest laterally extending projections. The ends of the prosthesis including the projections may be referred to as crowns or flanges, as desired, and may form a seal against the ostium formed into the blood vessel.

Figure 1C:
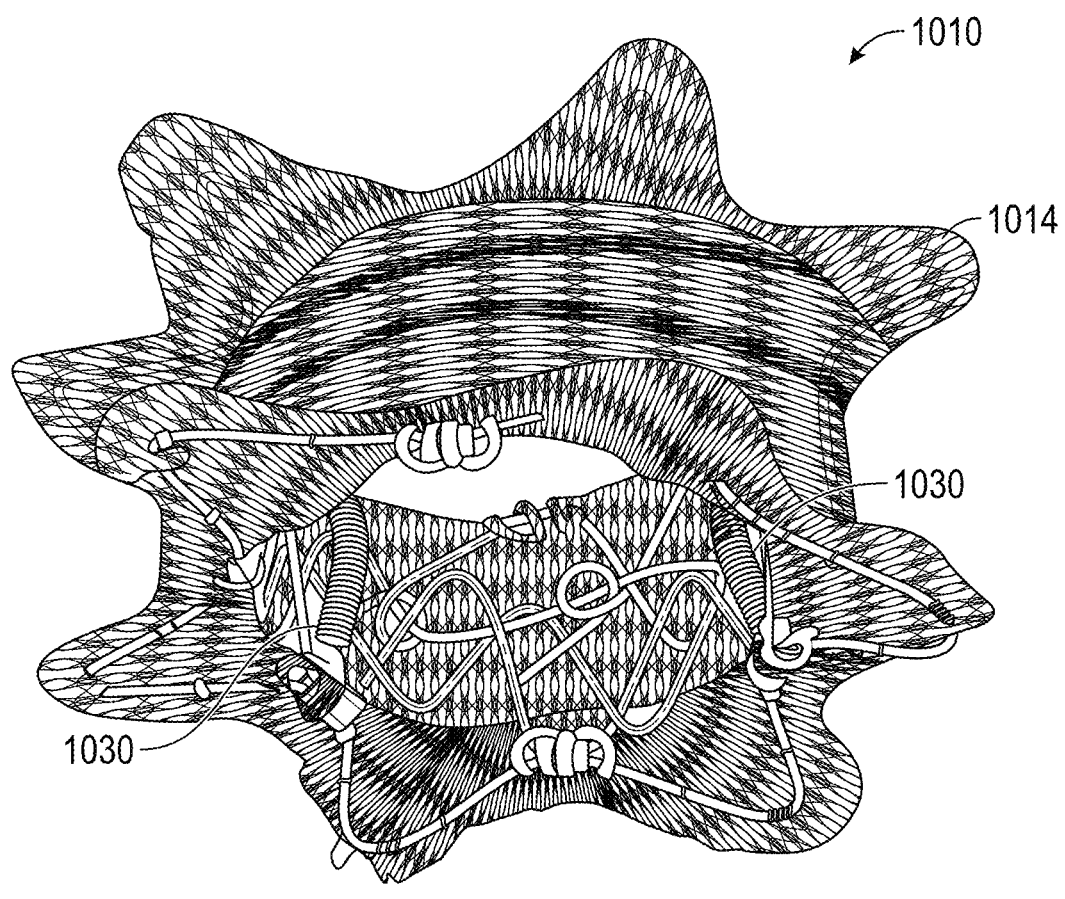
FIG. 1C illustrates the prosthesis for a Potts shunt of FIGS. 1A and 1B.
Figure 2C:
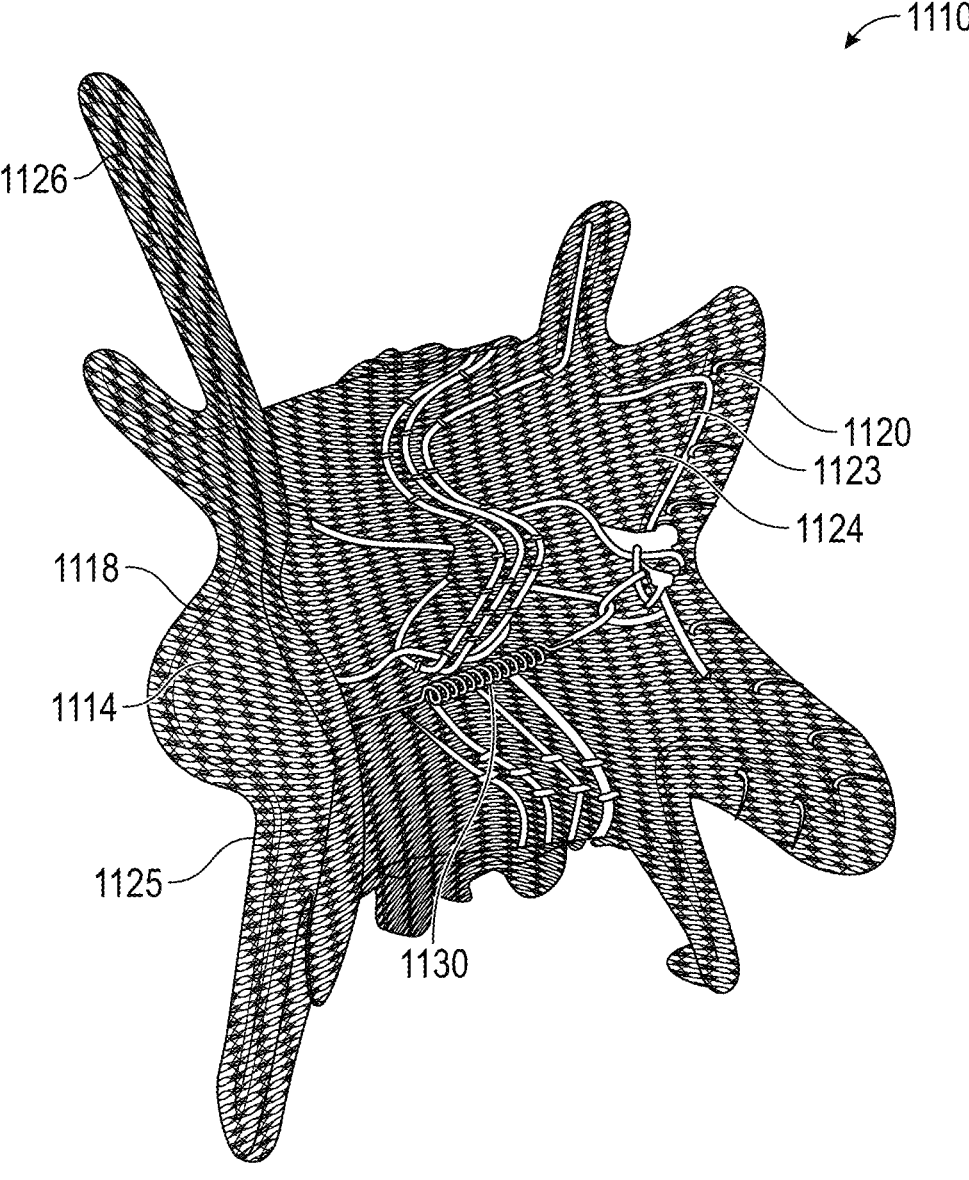
Figure 3A:
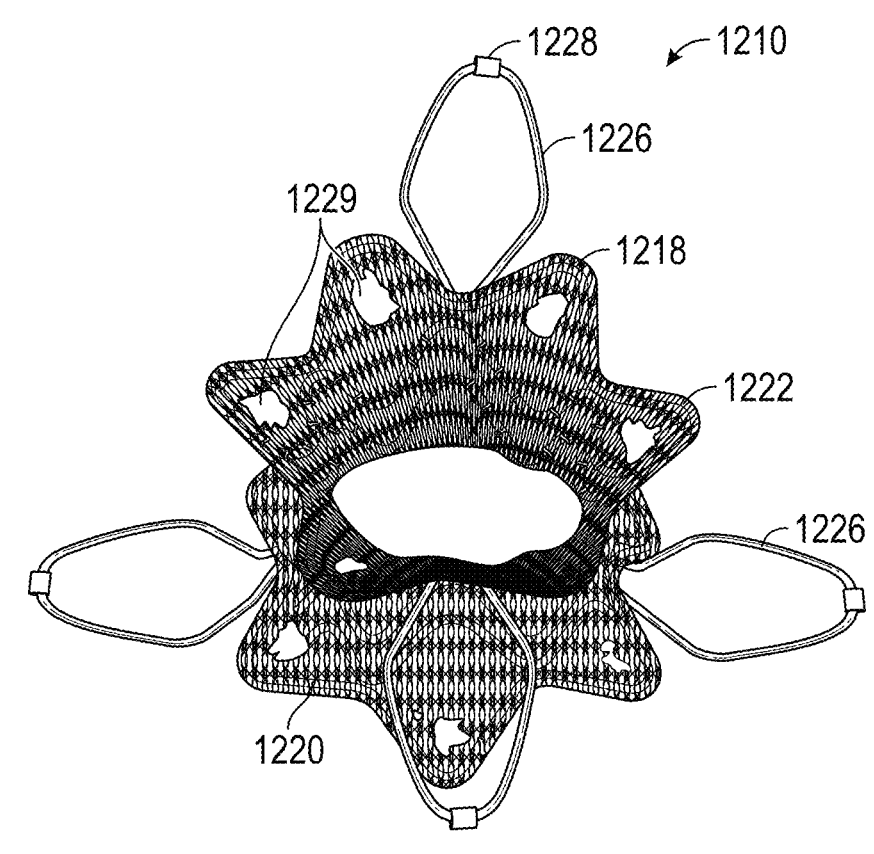
FIGS. 3A and 3B illustrate a prosthesis for a Potts shunt, in accordance with an embodiment of the disclosure.
Figure 3B:
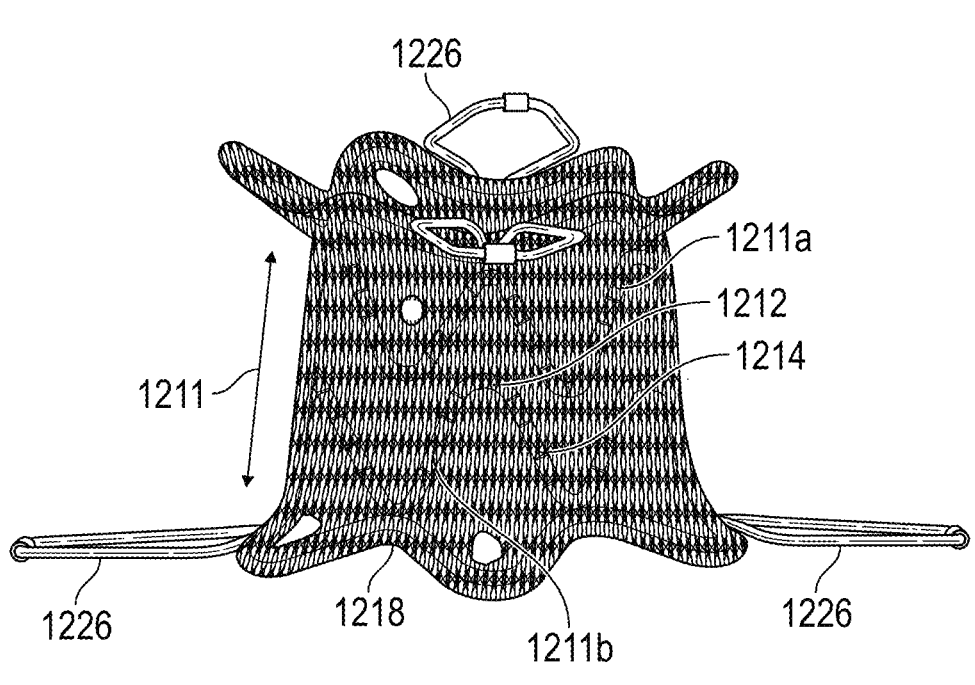

FIGS. 1A and 1B illustrate a the structural frame of a prosthesis for a Potts shunt procedure, also referred to herein as a "Potts shunt", in accordance with a first embodiment of the present disclosure. FIG. 1C illustrates the prosthesis for a Potts shunt of FIGS. 1A and 1B. FIG. 2A illustrate a the structural frame of a prosthesis for a Potts shunt, in accordance with a second embodiment. FIGS. 2B, and 2C illustrate the prosthesis for a Potts shunt of FIG. 2A. FIGS. 3A and 3B illustrate a prosthesis for a Potts shunt, in accordance with a third embodiment.

In the embodiment of FIGS. 1A-1C, the prosthesis 1010 comprises a frame 1012 and fabric 1014. As shown, the frame 1012 may be a knit frame. The frame 1012 can be provided with an active retraction mechanism, such as one or more tension springs 1030 coupled to the frame 1012 or elastic material, preferably located inside the fabric 1014. The frame 1012 comprises a tubular structure 1011 and top and bottom (or proximal and distal) crowns 1013. The center of the tubular body 1011 forms a lumen. In the embodiment shown, each crown includes a plurality of evenly spaced laterally extending projections or tabs 1022. The crowns form proximal and distal flanges of the prosthesis 1010. Each crown may comprise an undulating, star-shaped circumferential wire frame, wherein the illustrated embodiment resembles a six pointed star. The undulating, star-shaped circumferential wire frame of the crown can be integral with or may be coupled to the tubular structure, such as to fabric that form a membrane over the structure, or to adjacent strut rings. Each crown can be configured to move or flex with respect to the tubular structure.

The crowns may comprise top and bottom wires 1018, 1020, respectively, that have outwardly extending, generally uniformly sized, projections 1022. In the embodiment shown, the projections 1022 project laterally from the tubular structure 1011 at approximately 45 degrees. In other embodiments, the projections 1022 may project generally perpendicular to the tubular structure 1011 or at a different angle from the tubular structure 1011.

As further illustrated in FIG. 1A, the top wire 1018 is coupled to a first undulating intermediate strut ring 1011b wherein the apices of the wire 1011b are collocated with the inner apices of the top wire 1018. The wire 1018 and wire 1011b are joined by and fixated to one another by a plurality of tubular crimps 1019, but other means can be used, such as sutures wrapped around the members, and/or by stitching each wire to a tubular fabric, wherein the wires can flex more if attached only to the fabric rather than each other. FIG. 1A further illustrates a second intermediate strut ring 1011c that is shaped similar to ring 1011b, but is interwoven with ring 1011b to permit the prosthesis to grow or shorten in length, wherein the wires 1011b, 1011c slide over each other when moving in this fashion. A fourth strut ring 1011d, shaped essentially the same as wires 1011a, b, and c, is interwoven with ring 1011c on an upward side, and is crimped to ring 1020 at its lower side. The net result is a frame that can collapse axially as illustrated in FIG. 1B.

In the embodiment of FIGS. 1A-1C, the membrane (or fabric) 1014 is provided around the outside of the frame 1012. Alternatively, the membrane 1014 may be provide inside the frame 1012. The fabric 1014 may be coupled to the frame 1012 along top and bottom wires 1018, 1020 of the frame. Such connection may be by, for example, stitching the fabric along the top and bottom wires 1018, 1020. The fabric wrapped crowns form sealing flanges configured and arranged to facilitate sealing the prosthesis against a concave walls of a first vessel and a second vessel.

In the embodiment of FIGS. 2A-2C, the prosthesis 1110 comprises a connected wire frame 1112 and fabric 1114. As shown, the frame 1112 may be a knit frame. The frame 1112 is provided with an active retraction mechanism, such as springs, outside of the fabric 1114. The frame 1112 comprises a tubular structure 1111 and top and bottom (or proximal and distal) crowns 1123, 1125. The center of the tubular structure 1111 forms a lumen. The tubular structure 1111 is formed by a plurality of wires 1121. The wires 1121 may be zig zagged, undulating, or generally have a non-linear shape.

In the embodiment shown, each crown includes a plurality of evenly spaced laterally extending projections or tabs. The crowns form proximal and distal flanges of the prosthesis 1110. Each crown may comprise an undulating, star-shaped circumferential wire frame. The undulating, star-shaped circumferential wire frame of the crown can be integral with or may be coupled to the tubular structure. Each crown can be configured to move or flex with respect to the tubular structure. The crowns 1123, 1125 have a plurality of short projections and long projections, each projection generally extending laterally from a central axis of the tubular structure 1111. In the embodiment shown, each crown 1123, 1125 has four short projections 1124 and two long projections 1126. The long projections 1126 may be referred to as paddles. The paddles of the top crown 1118 are oriented about 180 degrees with respect to one another and 90 degrees offset from the paddles of the bottom crown 1120 about a longitudinal axis of the prosthesis. Rather than two long projections 1126, if desired, three such long projections can be provided spaced 120 degrees apart that are separated by and interdigitated with the smaller projections. If so equipped, the long projections on the top ring can align with the lower ring, or be mutually offset by 60 degrees, for example. Finally, it will be appreciated that a shunt can be provided that includes a first flange as depicted with two long projections on one end, and three long projections on the second end. One, two, or three tension springs 1130 can be provided to cause the prosthesis 1110 to shorten longitudinally and resist a tensile axial force.

The membrane or fabric 1114 is provided along the inside the frame 1112. In alternative embodiments, the membrane 1114 may be provided along the outside of the frame 1112. The fabric 114 may be coupled to the frame 1112 by, for example, weaving the fabric along the top and bottom crown rings 1118, 1120. The fabric wrapped crowns form sealing flanges configured and arranged to facilitate sealing the prosthesis against a concave walls of a first vessel and a second vessel. The paddles 1126 extend laterally behind the sealing flanges and are configured and arranged to resist being pulled through the vessel wall.

In the embodiment of FIGS. 3A and 3B, a prosthesis 1210 is illustrated that comprises a frame 1212 and membrane or fabric 1214. No active retraction mechanism is illustrated in this embodiment, but could be provided if desired. The frame 1212 comprises a tubular structure 1211, crowns 1218, 1220, and paddles 1226. The crowns 1218, 1220 have outwardly extending, generally uniformly sized, tabs or projections 1222. The center of the tubular structure 1211 forms a lumen. In the embodiment shown, each crown includes a plurality of evenly spaced laterally extending projections or tabs 1222 that in turn help define openings 1229 that can accommodate a tether that is threaded through the openings that help hold the prosthesis in a delivery configuration when tension is applied to the tether. The tether can also be used to retrieve the prosthesis during implantation if it does not fit properly.

The structural framework of the prosthesis in the main tubular portion is formed by two undulating strut rings 1211a, 1211b having six upwardly and downwardly pointing apices. These wings are woven to or sewn to the membrane material 1214. The material 1214 can be provided on the insider and the outside of the prosthesis 1210. The crown rings 1218, 1220 can be attached to the upper and lower rings 1218, 1220 by clips or crimps, by suturing or stitches, or rings 1218 1220 can be joined by stitching or weaving to the fabric 1214. The paddles 1226 are preferably crimped to the crown(s) 1218, 1220 and/or the rings 1211a/1211b.

The crowns form proximal and distal flanges of the prosthesis 1210. Each crown may comprise an undulating, star-shaped circumferential wire frame. The undulating, star-shaped circumferential wire frame of the crown can be integral with or may be coupled to the tubular structure. Each crown can be configured to move or flex with respect to the tubular structure.

The fabric 1214 can be provided outside of the frame and may be woven to top and bottom crowns 1218, 1220. The prosthesis 1210 can have discrete sizing for variable lengths. The fabric wrapped crowns 1218, 1220 form sealing flanges configured and arranged to facilitate sealing the prosthesis against a concave walls of a first vessel and a second vessel.

As shown, two paddles 1226 may be provided adjacent the top crown 1218, the two paddles 1226 being oriented about 180 degrees with respect to each other about a longitudinal axis of the prosthesis. Similarly, two paddles 1226 may be provided adjacent the bottom crown 1220, the two paddles 1226 being oriented about 180 degrees with respect to one another and 90 degrees offset from the top paddles about a longitudinal axis of the prosthesis. The paddles 1226 extend laterally behind the sealing flanges, or crowns, and are configured and arranged to resist being pulled through the vessel wall. Similar to embodiment 1110, three paddles 1226 can be provided rather than two if so desired.

Figures 4A, 4B, 5A, 5B, 6A, 6B:
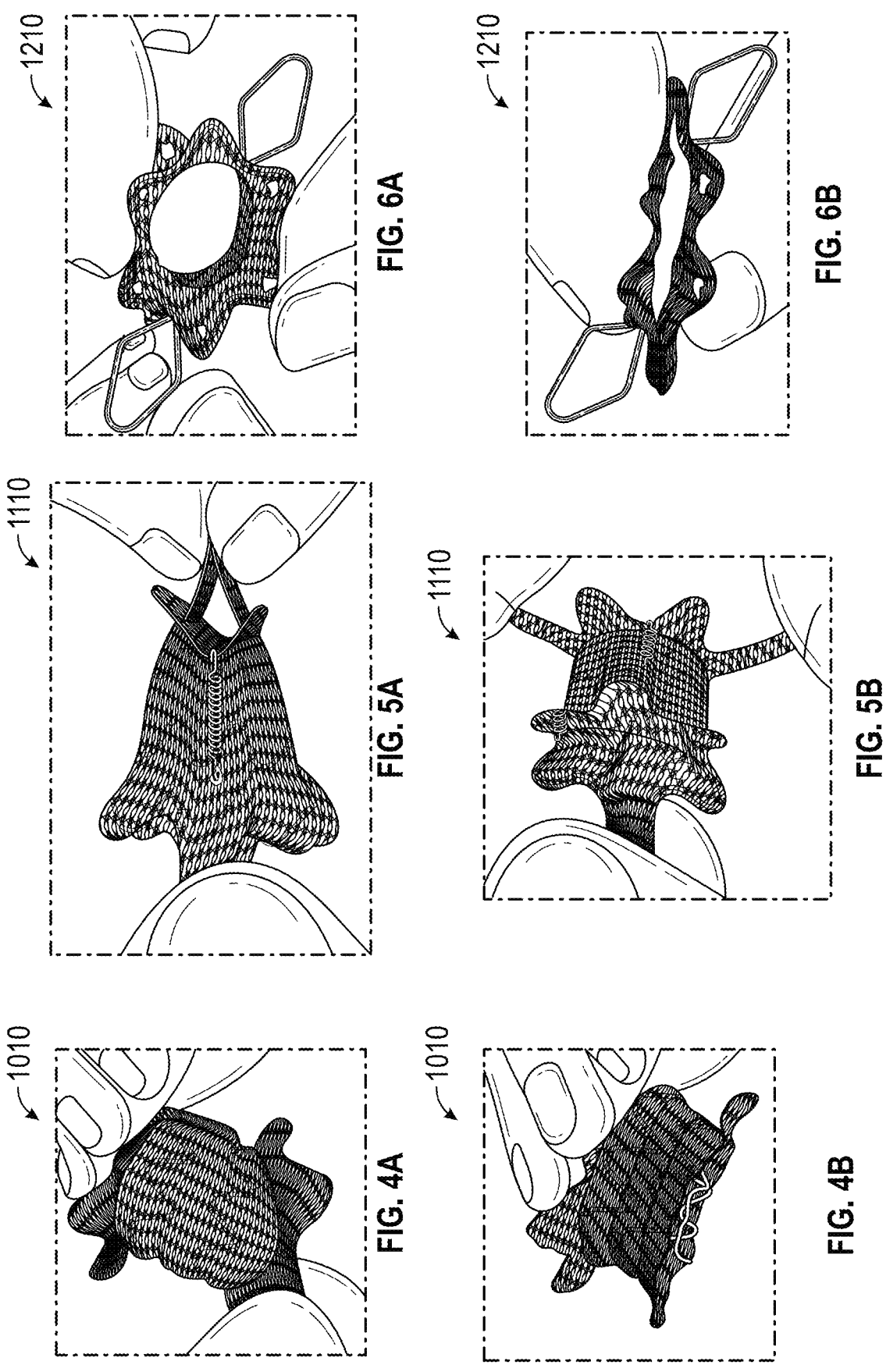
FIGS. 4A-4B illustrates handling of the prosthesis of FIGS. 1A-1C.
FIGS. 5A-5B illustrates handling of the prosthesis of FIGS. 2A-2C.
FIGS. 6A-6B illustrates handling of the prosthesis of FIGS. 3A-3B.

FIGS. 4A-6B illustrate handling of the exemplary prostheses. FIGS. 4A-4B illustrate the prosthesis 1010 of FIGS. 1A-1C in a stretched and collapsed configuration. Similarly, FIGS. 5A-5B illustrate prosthesis 1110 in a stretched and collapsed configuration, and FIGS. 6A-6B illustrate prosthesis 1210 in a radially expanded and collapsed configuration.

Figure 7:
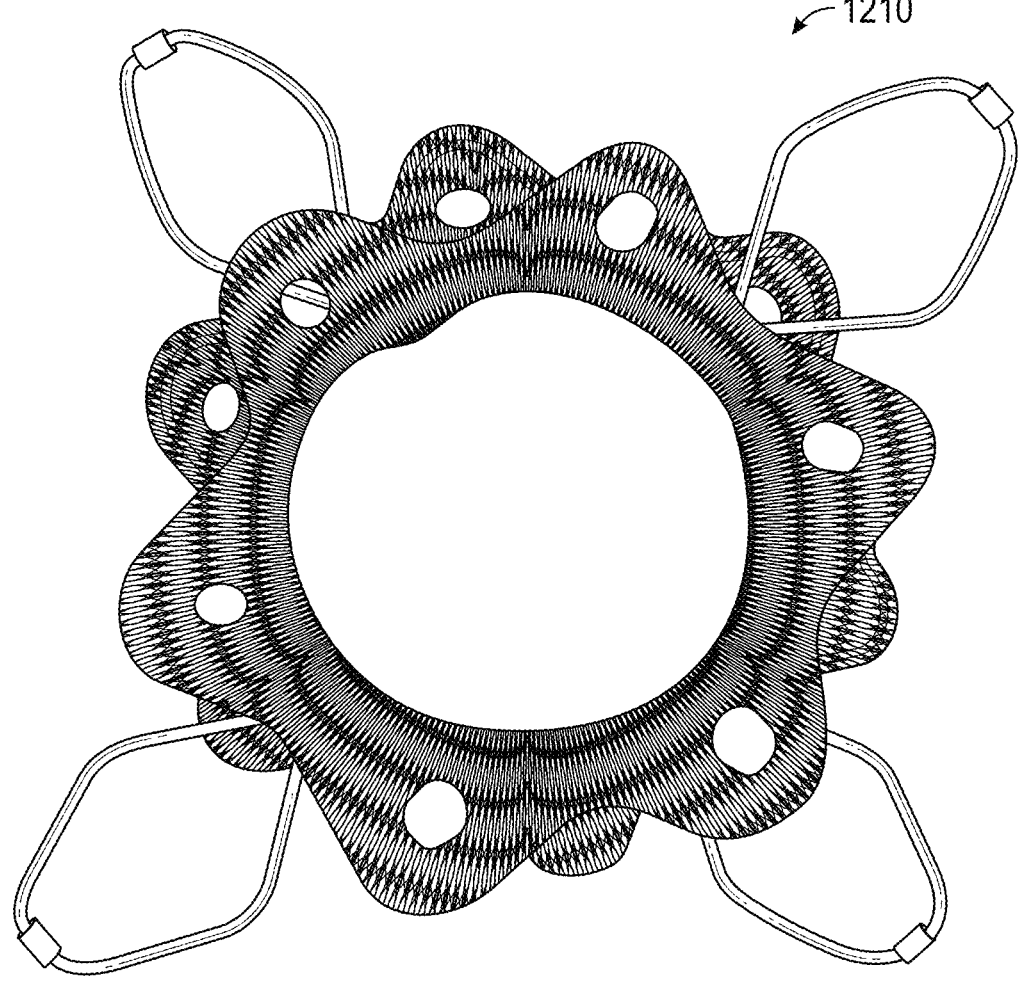
FIG. 7 is a top view of the prosthesis of FIGS. 3A-3B.
Figure 8:
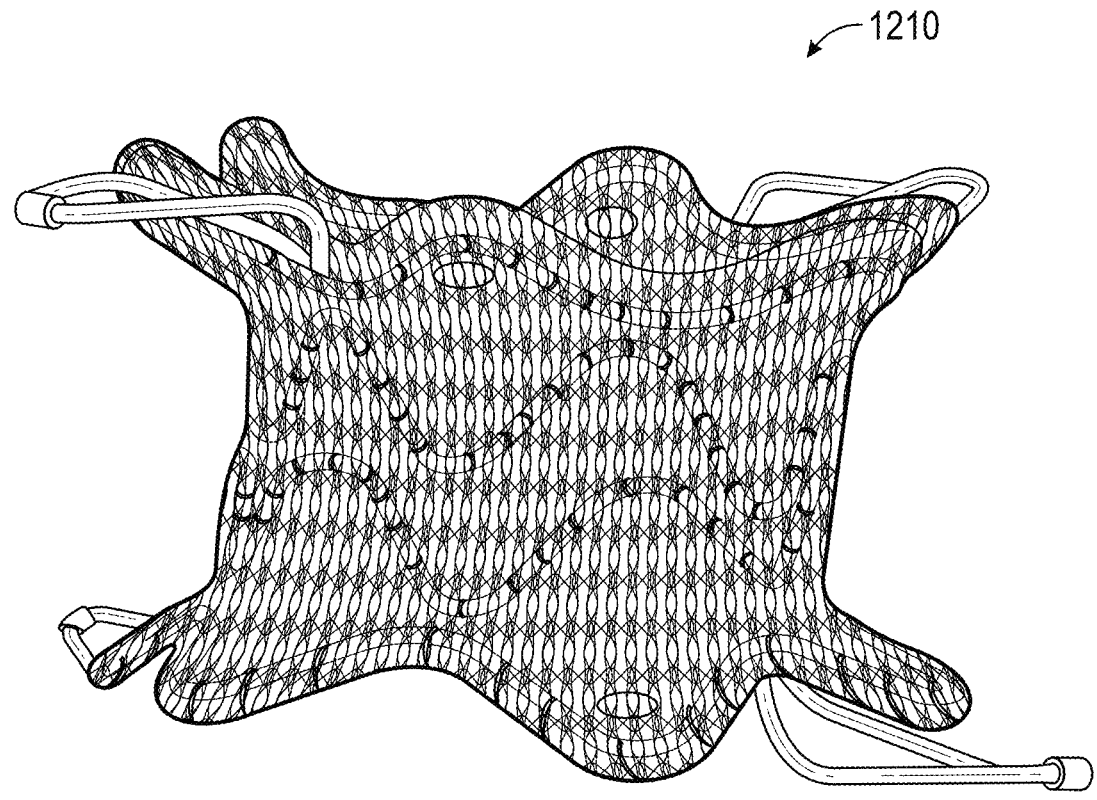
FIG. 8 is a side view of the prosthesis of FIGS. 3A-3B.

FIGS. 7-8 illustrate additional detail of Concept 3 (shown in FIGS. 3A and 3B). FIG. 7 illustrates a top view of a prosthesis, in accordance with such embodiment. FIG. 8 illustrates a side view of the prosthesis of FIG. 7.

FIGS. 7 and 8 illustrate dimensions including lumen diameter (A), outer diameter (B), body length (C), and overall length (D). In an exemplary embodiment, the lumen diameter (A) may be between about 8 mm and about 12 mm, or approximately 10 mm. In an exemplary embodiment, the outer diameter (B) may be between about 8.5 mm and about 12.5 mm, or approximately 10.7 mm. In an exemplary embodiment, the body length (C) may be between about 3 mm and about 7 mm, or approximately 5 mm. In an exemplary embodiment, the overall length (D) may be between about 6 mm and about 10 mm, or approximately 7.8 mm. Additional dimensions include crown outer diameter (peak to peak) and paddle length (peak to peak). The crown outer diameter may be, for example, between about 13 mm and 17 mm, or approximately 15 mm. The paddle length may be, for example, between about 24 mm and 28 mm, or approximately 26 mm.

In some embodiments, an end of the prosthesis (e.g., 1010, 1110, 1210) can receive a tether. As used, the end receiving the tether may be a proximal end, meaning an end closest to the surgeon. The end receives the tether and the tether is routed through a side surface of the tubular member (for example, between wires of the tubular member) and through the membrane material (for example, between an opening defined in the membrane material). The tether(s) are withdrawn proximally through a tube (e.g., a sheath) that also passes a core member therethrough that forms the core, or push rod of the delivery system. The core is slidably disposable with respect to the sheath. By advancing the core member with the prosthesis mounted thereto distally outwardly of the sheath, the prosthesis can self-expand, or be expanded by a balloon. However, if the tether is tensioned, it can cause the proximal end of the prosthesis to collapse radially inwardly such that the prosthesis can be withdrawn into the sheath. While adjacent undulating rings of the prosthesis particularly near the distal end of the prosthesis can be connected to each other (e.g., by sewing), they can also be kept independent of one another, and be attached to an inner and/or outer tubular fabric layer. The rigidity of the prosthesis is selected and/or configured to provide a desired performance. Thus, the distal end can be relatively rigid to maintain an opening in the wall of a vessel or other organ in an open state that the prosthesis traverses through by resisting the force of the vessel wall to want to "close" the hole in itself. The proximal region is less rigid and can accommodate increasing vessel curvature of the vessel that it is mounted in.

Figures 9, 10:
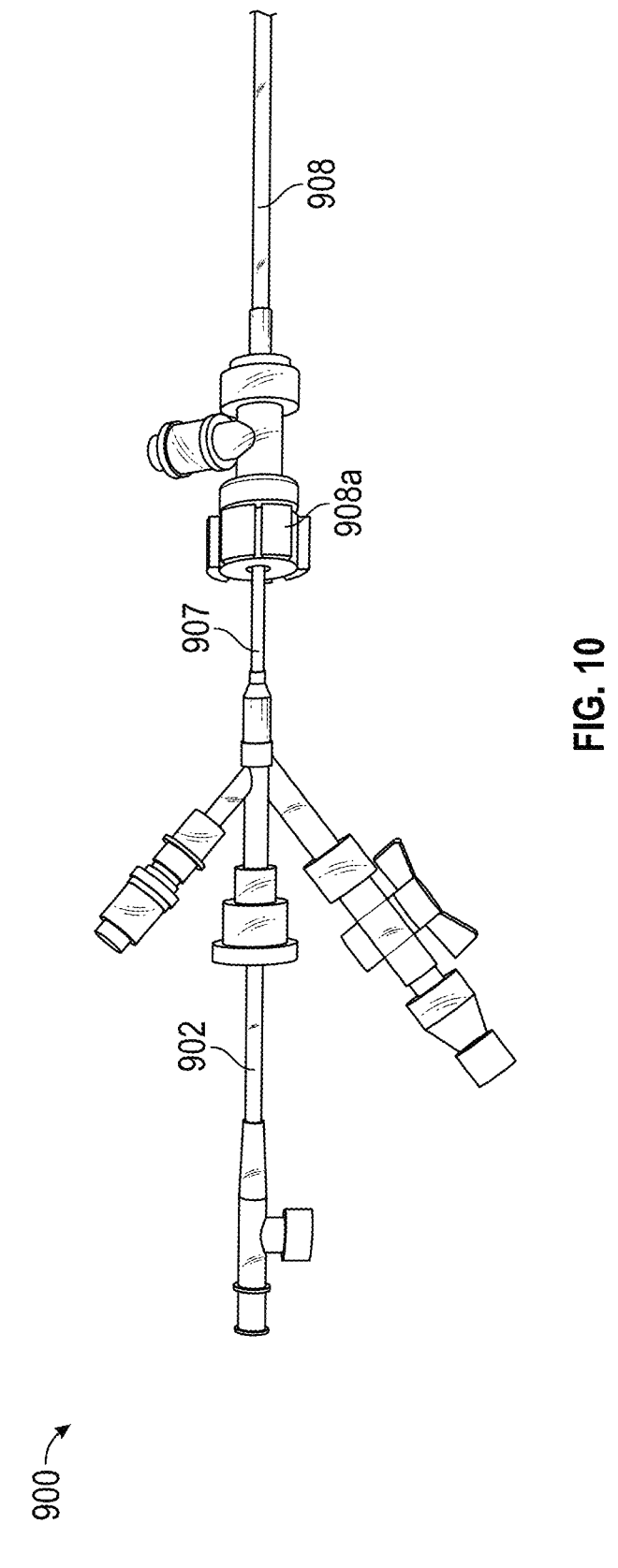
FIG. 9 is a close up view of a distal section of an illustrative delivery system for deploying a prosthesis for a Potts shunt.
FIG. 10 is a close up view of a proximal section of an illustrative delivery system for deploying a prosthesis for a Potts shunt.

An exemplary delivery system 900 for deploying a prosthesis for a Potts shunt is shown in FIGS. 9 and 10. FIG. 9 illustrates a distal end portion of the delivery system, which is based on and built on top of an innermost tube 902 made, for example, from a polymer such as PEEK, that runs to the distal end of the delivery system and forms a guidewire lumen therethough (not shown). An atraumatic tapered distal tip 904 is attached to the distal end portion of the innermost tube 904, that includes a reduced diameter section 904*a* to receive a distal end of sheath 908 thereover prior to delivery. An inflatable member 906 can be provided just proximal to the tip 904 that can be filled with an inflation fluid via an inflation channel (not shown). The prosthesis (1010, 1110, 1210, for example) can be mounted and crimped, if needed around the balloon, and covered by the sheath 908. Sheath 908 terminates on a proximal end in the form of hub 908*a* that can be slid with respect to inner member 902. An intermediate tubular member can be provided for stiffness, and to define an annular space around tube 902 to permit passage of fluids and the like. FIG. 10 shows a series of hubs and handles that illustrate how the tubular members 902, 907, 908 terminate on the proximal end of the catheter 900.

FIG. 11 illustrates a block diagram of a method 1300 for placing a Potts shunt, in accordance with one embodiment. The transfemoral artery is accessed 1310, for example, using a transcatheter pacing (TPS) delivery system. Access via the transjugular or transfemoral vein is made 1320 for the snare. A snare is placed in the left pulmonary artery (LPA) 330. A crossing is done from descending aorta (DAo) to left pulmonary artery (LPA) 330, for example using an electrosurgical guidewire. An electrosurgical guidewire for such crossing may be, for example, a 0.014" guidewire. The electrosurgical guidewire is exchanged for a larger guidewire 1340, such as a 0.035" guidewire. The transcatheter pacing delivery system is loaded over the lager guidewire 1350. The Potts shunt is deployed bridging from the descending aorta to the left pulmonary artery.

Figure 12A:
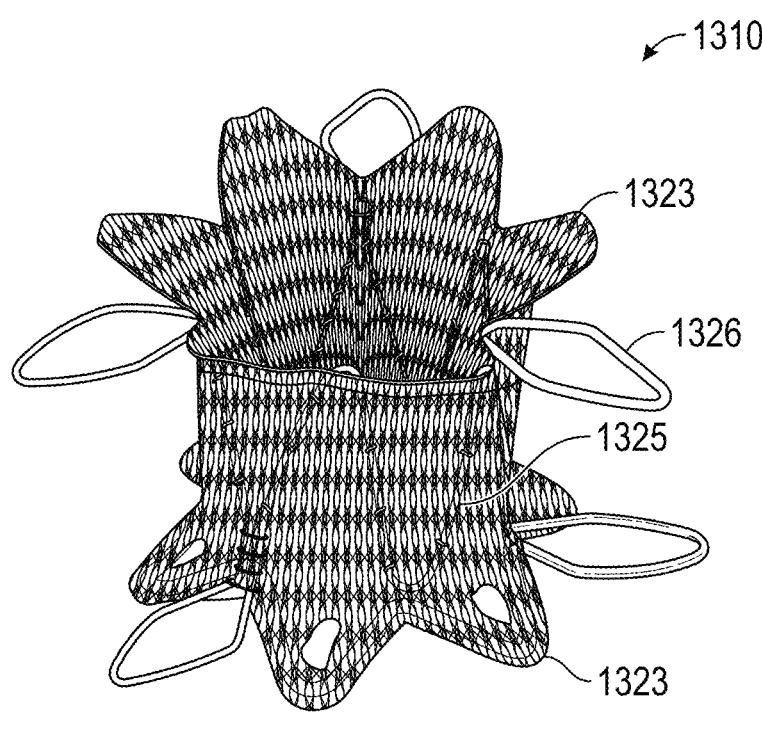
FIGS. 12A-12B illustrate a Potts shunt, in accordance with an embodiment of the disclosure.
Figure 12B:
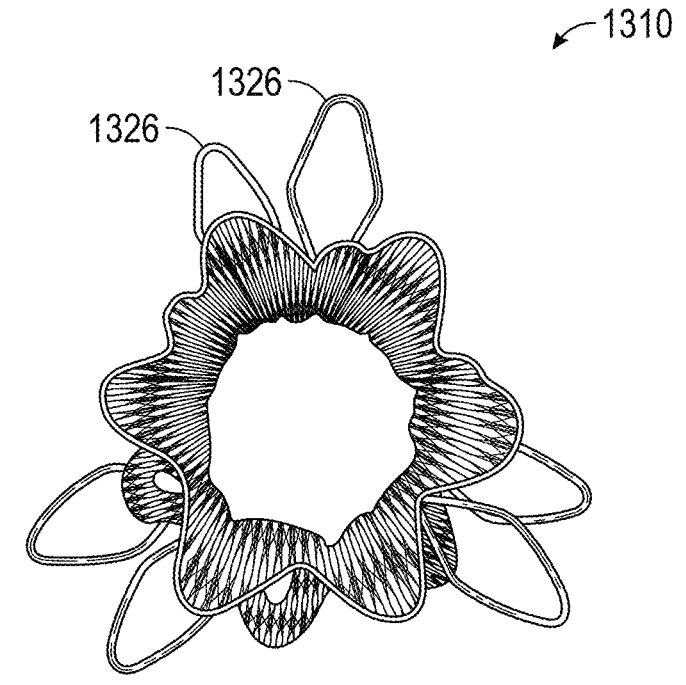

FIGS. 12A-12B illustrate still a further prosthesis 1310 that is of fixed axial length and has a frame formed by a single strut ring 1325 attached at an upper end to a star shaped flange wire 1323 and at a lower end to another such wire 1323. Three paddles 1326 are attached to an upper end of the prosthesis, and three more are attached to a lower end of the prosthesis. As illustrated, the apices of the wires 1323 are rotationally offset from one another by 30 degrees, as are the paddles 1326 on the top and bottom of the prosthesis. Fabric is provided to cover the framework, and holes are defined at the lower end of the prosthesis through the fabric proximate the ring 1323 to permit routing of a tether therethrough. As such, the lower end of the prosthesis 1310 is preferably oriented toward the proximal end of the delivery system so that the tether can be used to remove the prosthesis if the installation does not go as planned. Once the installation is correct though, one end of the tether loop routed through the openings of the prosthesis can be released, and the other end pulled, to fully remove the tether from the patient.

In general, it will be appreciated that any of the prostheses disclosed herein can further include at least one elastic body (e.g., tension coil spring) that causes the tubular prosthesis to shorten in length when unconstrained. The at least one elastic body can include at least one tension coil spring that defines a lumen along its length. A central longitudinal axis of the at least one tension coil spring is preferably coincident (or at least concentric) with a longitudinal axis of the prosthesis. Thus, the tubular prosthesis can be of adjustable telescoping length. Preferably, the inside diameter of the prosthesis remains substantially unchanged when the prosthesis is adjusted in length. The at least one tension coil spring can actually include a plurality of tension coil springs that may be adjacent to or concentrically located with respect to one another.

Figure 13:
FIG. 13 illustrates a further implementation of a delivery system for a Potts shunt in accordance with the present disclosure.

The disclosure further provides a delivery system including a prosthesis as described elsewhere herein mounted thereon in FIG. 13.

As depicted, the delivery system includes an inflatable member (balloon catheter) mounted on the elongate inner core member, and the prosthesis (e.g., 1110) is mounted around the elongate inner core member. A retractable sheath is also provided having a proximal end and a distal end. The retractable sheath is slidably disposed with respect to, and depending on its position along the elongate core member, selectively covers, the prosthesis and at least a part of the inflatable member. The delivery system can further include a first actuator (not shown) configured and arranged to advance the sheath proximally with respect to the elongate inner core, inflatable member, and prosthesis. A second actuator can be coupled to a reservoir of fluid, and a third actuator can be used to manage the tension on the tether.

In particular, the innermost member is similar to FIG. 9, wherein a balloon catheter forms the innermost catheter. This balloon catheter can be moved with respect to an intermediate catheter by sliding it with respect to the intermediate catheter using the balloon catheter actuator. The intermediate catheter is coupled to the retractable sheath that covers the prosthesis. The actuator of the intermediate catheter is slid proximally to expose the prosthesis, and the tether that runs through the holes on the proximal end of the prosthesis are managed (held in tension, for example) in the actuator for the intermediate catheter. The outer deliver catheter is received over the sheath of the intermediate catheter and can be used to help facilitate the delivery of the inner two catheters to the site.

In some embodiments, the prosthesis can be mounted at least partially over and surrounding the inflatable member. For example, a distal portion of the prosthesis can be mounted over the inflatable member, a proximal portion of the prosthesis can be mounted over the inflatable member, or a central portion of the prosthesis can be mounted over the inflatable member. If desired, the prosthesis can be mounted on the elongate inner core member proximally, or distally, with respect to the inflatable member.

An exemplary method in accordance with the disclosure includes providing a delivery system as described herein, delivering a distal end of the delivery system to a target location through the ostium of the first concave vessel wall, withdrawing the sheath proximally to expose the prosthesis, positioning the distal end of the prosthesis in the ostium so that the sealing flange and the at least one laterally extending projection are inside the first concave vessel wall and the elongate compliant tubular body extends through the ostium outside of the first vessel, actuating the second actuator to cause the inflatable member to expand, and expanding the distal end of the tubular prosthesis using the balloon to fit it into the ostium and to shape the sealing flange to fit against the first concave vessel wall.

If desired the inflatable member can be positioned distally with respect to the prosthesis, and the inflatable member can be inflated to outwardly flare the distal end of the prosthesis, as desired. The method can further include adjusting the length of the prosthesis to a desired length. The method can further include disposing a proximal end of the prosthesis inside of a second vessel. For example, the proximal end of the prosthesis can be mounted transversely through a second ostium formed in a wall of the second vessel to shunt the first vessel to the second vessel.

The devices and methods disclosed herein can be used for other procedures in an as-is condition, or can be modified as needed to suit the particular procedure. In view of the many possible embodiments to which the principles of this disclosure may be applied, it should be recognized that the illustrated embodiments are only preferred examples of the disclosure and should not be taken as limiting the scope of the disclosure.

What is claimed is:

1. A prosthesis having a proximal end, a distal end, and defining an axial direction from the proximal end to the distal end, the prosthesis comprising:

a proximal sealing flange configured and arranged to facilitate seating a proximal end portion of the prosthesis against an interior concave surface of a wall of a first vessel, wherein the prosthesis is configured to extend outwardly through an ostium formed through the wall of the first vessel when deployed, wherein the proximal sealing flange remains inside the ostium after deployment;

a distal sealing flange displaceable from the proximal sealing flange along the axial direction, the distal sealing flange being configured and arranged to facilitate seating a distal end portion of the prosthesis against an interior concave surface of a wall of a second vessel, wherein the prosthesis is configured to extend outwardly through an ostium formed through the wall of the second vessel when deployed, wherein the distal sealing flange remains inside the ostium after deployment; and a first circumferential undulating strut ring formed from a first undulating filament disposed axially between the proximal sealing flange and the distal sealing flange;

a second circumferential undulating strut ring formed from a second undulating filament disposed axially between the proximal sealing flange and the distal sealing flange, the filament of the second circumferential undulating strut ring being woven and wrapped around the filament of the first circumferential undulating strut ring about a circumference of the prosthesis, wherein the filament of the first circumferential undulating strut ring and the filament of the second circumferential undulating strut ring are configured to slide over each other along the axial direction to permit the prosthesis to collapse along the axial direction into a nested configuration.

2. The prosthesis of claim 1, further comprising at least one tension coil spring connecting the proximal sealing flange to the distal sealing flange to cause the prosthesis to collapse into the nested configuration, the at least one tension coil spring being disposed adjacent to each of the first circumferential undulating strut ring and the second circumferential undulating strut ring.

3. The prosthesis of claim 2, wherein the at least one tension coil spring includes a plurality of coil springs spaced circumferentially apart from each other about a circumference of the prosthesis.

4. The prosthesis of claim 1, further comprising a membrane covering the prosthesis.

5. The prosthesis of claim 4, wherein the proximal sealing flange and the distal sealing flange are each formed from an undulating wire forming a star shape, the undulating wire forming a plurality of radially outwardly extending lobes interspersed by a plurality of radially inwardly extending vertices, and further wherein each radially outwardly extending lobe is covered by the membrane material.

6. The prosthesis of claim 5, wherein a pair of laterally opposing lobes on each of the proximal sealing flange and the distal sealing flange are larger than other lobes on each said respective sealing flange disposed between the pair of laterally opposing lobes.

7. The prosthesis of claim 5, wherein each said flange includes six lobes, wherein each said flange includes three relatively long lobes mutually separated by an angular displacement of about 120 degrees that are interdigitated with three relatively short lobes mutually separated by an angular displacement of about 120 degrees.

8. The prosthesis of claim 5, wherein each the proximal sealing flange and the distal sealing flange each includes a further pair of laterally opposing radially outwardly directed projections, wherein each said further pair of projections is formed from a wire loop that is not covered by the membrane material.

9. The prosthesis of claim 8, wherein the further pair of projections coupled to the proximal sealing flange are located in an orientation that is rotated 90 degrees about a central axis of the prosthesis with respect to further pair of projections coupled to the distal sealing flange.

10. A prosthesis having a proximal end, a distal end, and defining an axial direction from the proximal end to the distal end, the prosthesis comprising:

a proximal sealing flange configured and arranged to facilitate seating a proximal end portion of the prosthesis against an interior concave surface of a wall of a first vessel, wherein the prosthesis is configured to extend outwardly through an ostium formed through the wall of the first vessel when deployed, wherein the proximal sealing flange remains inside the ostium after deployment;

a distal sealing flange displaceable from the proximal sealing flange along the axial direction, the distal sealing flange being configured and arranged to facilitate seating a distal end portion of the prosthesis against an interior concave surface of a wall of a second vessel, wherein the prosthesis is configured to extend outwardly through an ostium formed through the wall of the second vessel when deployed, wherein the distal sealing flange remains inside the ostium after deployment;

a plurality of undulating circumferential strut rings disposed axially between the proximal sealing flange and the distal sealing flange; and at least one tension coil spring connecting the proximal sealing flange to the distal sealing flange to cause the prosthesis to collapse into an axially shortened configuration, the at least one tension coil spring being disposed along an axial direction alongside and radially displaced with respect to each of the plurality of undulating strut rings.

11. The prosthesis of claim 10, further comprising a membrane covering the prosthesis.

12. The prosthesis of claim 11, wherein the proximal sealing flange and the distal sealing flange are each formed from a plurality of radially outwardly extending lobes, and further wherein each radially outwardly extending lobe is covered by the membrane material.

13. The prosthesis of claim 11, wherein each the proximal sealing flange and the distal sealing flange each includes a further plurality of radially outwardly directed projections, each said further plurality of radially outwardly directed projections being formed from a wire loop that is not covered by the membrane material.

14. The prosthesis of claim 13, wherein the further plurality of radially outwardly directed projections coupled to the proximal sealing flange are located in an orientation that is rotated about a central axis of the prosthesis with respect to the further plurality of radially outwardly directed projections coupled to the distal sealing flange.

15. The prosthesis of claim 1, wherein the filament of the first circumferential undulating strut ring is adjacent and coupled to the proximal sealing flange, and the second circumferential undulating strut ring is adjacent and coupled to the distal sealing flange.

16. The prosthesis of claim 2, wherein the at least one tension coil spring is disposed radially inwardly with respect to the first circumferential undulating strut ring.

17. The prosthesis of claim 2, wherein the at least one tension coil spring is disposed radially outwardly with respect to the first circumferential undulating strut ring.

18. The prosthesis of claim 10, wherein the at least one tension coil spring is disposed radially inwardly with respect to the plurality of undulating circumferential strut rings.

19. The prosthesis of claim 10, wherein the at least one tension coil spring is disposed radially outwardly with respect to the plurality of undulating circumferential strut rings.

* * * * *